US006353119B1

(12) United States Patent
Crispino et al.

(10) Patent No.: US 6,353,119 B1
(45) Date of Patent: Mar. 5, 2002

(54) PREPARATION OF 3-SUBSTITUTED-4-ARYLQUINOLIN-2-ONE DERIVATIVES

(75) Inventors: Gerard A. Crispino, Princeton; Shaopeng Wang, Basking Ridge; Jun Li, North Brunswick, all of NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/724,056

(22) Filed: Nov. 28, 2000

Related U.S. Application Data

(60) Provisional application No. 60/168,346, filed on Dec. 1, 1999.

(51) Int. Cl.$^7$ .................... C07D 307/02; C07D 307/08; C07D 215/20; C07D 215/36
(52) U.S. Cl. ...................... 549/156; 549/488; 549/489; 546/157
(58) Field of Search ................ 549/488, 489; 546/157, 156; 514/312

(56) References Cited

U.S. PATENT DOCUMENTS

| | | | | |
|---|---|---|---|---|
| 5,091,428 A | * | 2/1992 | Deloesi et al. | 514/231.5 |
| 5,200,422 A | | 4/1993 | Olesen et al. | 514/387 |
| 5,565,472 A | | 10/1996 | Hamanaka | 514/312 |
| 5,892,045 A | | 4/1999 | Sit et al. | 546/153 |
| 5,972,961 A | | 10/1999 | Hewawasam et al. | 514/312 |
| 6,184,231 B1 | * | 2/2001 | Hewawasam et al. | 549/157 |

FOREIGN PATENT DOCUMENTS

WO    WO 93/08800    5/1993 ................. 514/312

OTHER PUBLICATIONS

Ahmed, F. et al., "Some Features of the Spasmogenic Actions of Acetrylcholine and Histamine in Guinea–Pig Isolated Trachealis", *Br. J. Pharmacol.*, (1984) 82 227–233.

Baró, I. and Escande, D., "A $Ca^{2+}$–activated $K^+$ Current in Guinea–pig Atrial Myocytes", *Pflügers Archiv.*, (1989) 414 (Suppl. 1): S168.

Cook, N.S., "The Pharmacology of Potassium Channels and Their Therapeutic Potential", *Trends in Pharmacol. Sciences*, (Jan., 1988) 9: 21–28.

Quast, U. and Cook, N. S., "Moving Together: $K^+$ Channel Openers and ATP–sensitive $K^+$ Channels", *Trends in Pharmacol. Sciences*, (Nov., 1989) 10: 431–435.

Singer, J. J. and Walsh, J.V., "Characterization of Calcuim–activated Potassium Channels in Single Smooth Muscle Cells Using the Patch–clamp Technique", *Pflügers Archiv.*, (1987) 408: 98–111.

Olesen S.P., Munch E, Moldt P., and Drejer J. "Selective activation of $Ca^{2+}$–dependent $K^+$ channels by novel benzimidazolone", *European Journal of Pharmacology*, (1994) 251:53–59.

\* cited by examiner

*Primary Examiner*—Alan L. Rotman
*Assistant Examiner*—Raymond Covington
(74) *Attorney, Agent, or Firm*—Aldo A. Algieri

(57) ABSTRACT

The present invention relates to a process for the preparation of 3-substituted-4-arylquinolin-2-one derivatives from a substituted coumarin and using a photochemical cyclization method on a dihydrofuran intermediate.

9 Claims, No Drawings

PREPARATION OF 3-SUBSTITUTED-4-ARYLQUINOLIN-2-ONE DERIVATIVES

CROSS REFERENCE TO RELATED APPLICATION

This is a non-provisional application which claims the benefit of provisional application U.S. Ser. No. 60/168,346 filed Dec. 1, 1999.

FIELD OF THE INVENTION

The present invention provides a novel process for the preparation of 3-substituted-4-arylquinolin-2-one derivatives which are modulators of the large-conductance calcium-activated potassium (BK) channels and, therefore, useful in the protection of neuronal cells and diseases arising from dysfunction of cellular membrane polarization and conductance. The present invention also provides novel intermediates for the preparation thereof.

BACKGROUND OF THE INVENTION

Potassium channels play a key role in regulation of cell membrane potential and modulation of cell excitability. Potassium channels are largely regulated by voltage, cell metabolism, calcium and receptor mediated processes. [Cook, N. S., *Trends in Pharmacol. Sciences* (1988), 9, 21; and Quast, U., et al., *Trends in Pharmacol. Sciences* (1989), 10, 431]. Calcium-activated potassium ($K_{Ca}$) channels are a diverse group of ion channels that share a dependence on intracellular calcium ions for activity. The activity of $K_{ca}$ channels is regulated by intracellular $[Ca^{2+}]$, membrane potential and phosphorylation. On the basis of their single-channel conductances in symmetrical $K^+$ solutions, $K_{Ca}$ channels are divided into three subclasses: large conductance (BK)>150 pS; intermediate conductance 50–150 pS; small conductance<50 pS. Large-conductance calcium-activated potassium (Maxi-K or BK) channels are present in many excitable cells including neurons, cardiac cells and various types of smooth muscle cells. [Singer, J. et al., *Pflugers Archiv.* (1987) 408, 98; Baro, I., et al., *Pflugers Archiv.* (1989) 414 (Suppl. 1), S168; and Ahmed, F. et al., *Br. J. Pharmacol.* (1984) 83, 227].

Potassium ions play a dominant role in controlling the resting membrane potential in most excitable cells and maintain the transmembrane voltage near the $K^+$ equilibrium potential ($E_k$) of about −90 mV. It has been shown that opening of potassium channels shift the cell membrane potential towards the equilibrium potassium membrane potential ($E_k$), resulting in hyperpolarization of the cell. [Cook, N. S., *Trends in Pharmacol. Sciences* (1988), 9, 21]. Hyperpolarized cells show a reduced response to potentially damaging depolarizing stimuli. BK channels which are regulated by both voltage and intracellular $Ca^{2+}$ act to limit depolarization and calcium entry and may be particularly effective in blocking damaging stimuli. Therefore cell hyperpolarization via opening of BK channels may result in protection of neuronal cells.

A range of synthetic and naturally occurring compounds with BK opening activity have been reported. The avena pyrone extracted from avena sativa-common oats has been identified as a BK channel opener using lipid bi-layer technique [International Patent application WO 93/08800, published May 13, 1993]. In U.S. Pat. No. 5,200,422, issued Apr. 6, 1993 to Olesen, et al., a number of benzimidazole derivatives were disclosed as openers of BK channels by using single-channel and whole-cell patch-clamp experiments in aortic smooth muscle cells. Further work was reported by Olesen, et al., in *European J. Pharmacol.*, 251, 53–59 (1994).

Sit, et al., in U.S. Pat. No. 5,892,045, issued Apr. 6,1999, disclosed a series of 4-aryl-3-hydroxyquinolin-2-one derivatives, while Hewawasam, et al., in U.S. Pat. No. 5,972,961, issued Oct. 26, 1999, disclosed a series of 4-aryl-3-aminoquinolini-2-one derivatives which are openers of BK channels and useful in the treatment of disorders sensitive to potassium channel opening activity.

E. S. Hamanaka in U.S. Pat. No. 5,565,472, issued Oct. 15, 1996, discloses a number of 4-aryl-3-(heteroarylureido)-1,2-dihydro-2-oxo-quinoline derivatives which are inhibitors of acyl coenzyme A; cholesterol acyltransferase and are useful as hypolipidemic and antiatherosclerosis agents.

It is the object of the present invention to provide a useful, convenient and improved process for the preparation of certain 3-substituted-4-arylquinolin-2-one derivatives which are openers of the high-conductance calcium-activated potassium (BK) channels and the utility thereof is more fully described by Hewawasam, et al. in U.S. provisional application No. 60/111,079 filed Dec. 4, 1998.

SUMMARY OF THE INVENTION

The present invention provides a novel process for the preparation of 3-substituted-4-arylquinolin-2-one derivatives having the general formula

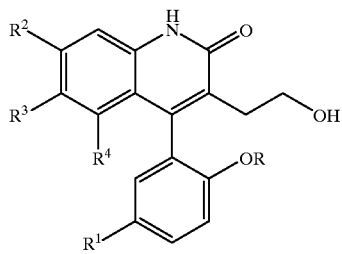

I wherein R, $R^1$, $R^2$, $R^3$ and $R^4$ are as defined below and which are openers of the large conductance calcium-activated $K^+$ channels also known as Maxi-K or BK channels useful for the treatment of disorders sensitive to potassium channel opening activity such as ischemia, stroke, convulsions, epilepsy, asthma, irritable bowel syndrome, migraine, traumatic brain injury, spinal cord injury, sexual dysfunction and urinary incontinence. More specifically, the present invention provides a unique process starting from a substituted coumarin and using a photochemical cyclization method.

DETAILED DESCRIPTION OF THE INVENTION

The present invention provides a novel process for the preparation of 3-substituted-4-arylquinolin-2-one derivatives which are modulators of the large-conductance calcium-activated potassium (BK) channels and have the general formula

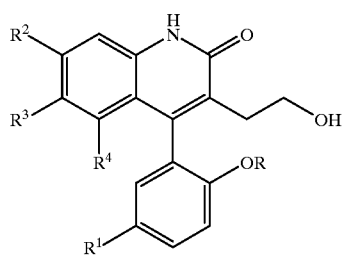

wherein R is hydrogen or methyl; $R^1$ is bromo, chloro or nitro; and $R^2$, $R^3$ and $R^4$ each are independently hydrogen, halogen, nitro or trifluoromethyl, provided $R^2$, $R^3$, and $R^4$ are not all hydrogen; or a nontoxic pharmaceutically acceptable salt thereof.

The present invention also provides useful intermediates of Formula VI

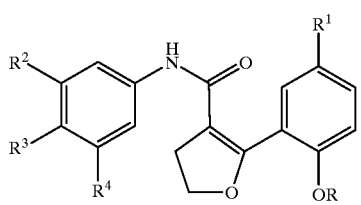

and to a process for the preparation thereof wherein R is hydrogen or methyl; $R^1$ is bromo, chloro or nitro; and $R^2$, $R^3$ and $R^4$ each are independently hydrogen, halogen, nitro or trifluoromethyl, provided $R^2$, $R^3$ and $R^4$ are not all hydrogen.

The term "nontoxic pharmaceutically acceptable salt" as used herein and in the claims is intended to include nontoxic base addition salts with inorganic bases. Suitable inorganic bases such as alkali and alkaline earth metal bases include metallic cations such as sodium, potassium, magnesium, calcium and the like. Unless otherwise specified, the term "halogen" as used herein and in the claims is intended to include bromine, chlorine, iodine and fluorine while the term "halide" is intended to include bromide, chloride and iodide anion.

Certain of the compounds of the present invention can exist in unsolvated forms as well as solvated forms including hydrated forms such as monohydrate, dihydrate, hemihydrate, trihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention. Certain compounds of Formula I can exist in two tautomeric forms. It should be appreciated by those skilled in the art that the quinoline ring can exist in an enol form. It is intended that both enolic tautomers of the compounds of Formula I are included within the scope of the present invention.

The following Reaction Scheme illustrates representative general procedures for the preparation of intermediates and methods for the preparation of compounds of formula I according to this invention. It should also be evident to those skilled in the art that appropriate substitution of both the materials and methods disclosed herein will produce the examples illustrated below and those encompassed by the scope of this invention.

REACTION SCHEME 1

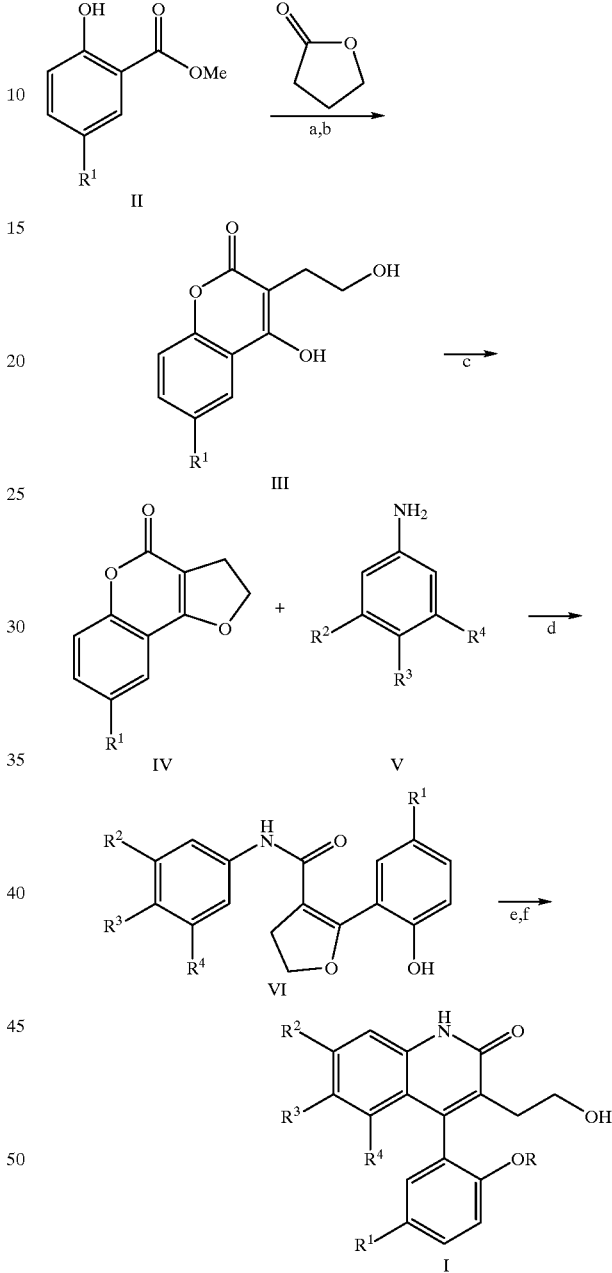

(a) LiHMDS/THF, −78° C. to RT
(b) 12N HCl
(c) pTSA, Toluene, reflux
(d) LiHMDS
(e) $(CH_3O)_2SO_2$, $K_2CO_3$
(f) hv, MeOH The preparation of compounds of Formula I is advantageously carried out by the reactions illustrated in Reaction Scheme 1. The coumarin compound of Formula III is preferably prepared by condensing γ-butyrolactone with the methyl ester of a substituted salicylic acid of Formula II which is then readily cyclized with a catalytic amount of acid to produce the benzopyran-4-one of Formula IV. Treatment of compound IV with a substituted aniline of Forumla V as illustrated in step (d) produced the dihydrofuran of Formula VI which is then optionally methylated with a methylating agent such as dimethyl sulfate. The dihydrofuran of Formula VI is then advantageously subjected to a photochemical cyclization in an inert organic solvent to afford the desired compound of Formula I.

In a preferred embodiment of the invention the compounds of Formula VI have the formula

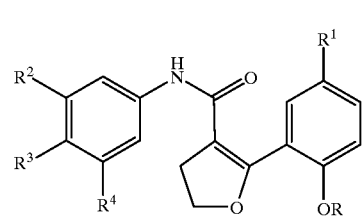

VI wherein R is hydrogen or methyl; $R^1$ is bromo, chloro or nitro; and $R^2$, $R^3$ and $R^4$ each are independently hydrogen, halogen, nitro or trifluoromethyl, provided $R^2$, $R^3$, and $R^4$ are not all hydrogen.

In another preferred embodiment, the invention provides a process for the preparation of a quinoline of compound of Formula I

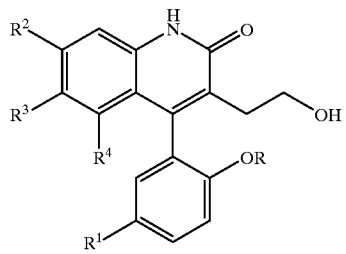

I wherein R is hydrogen or methyl; $R^1$ is bromo, chloro or nitro; and $R^2$, $R^3$ and $R^4$ each are independently hydrogen, halogen, nitro or trifluoromethyl, provided $R^2$, $R^3$, and $R^4$ are not all hydrogen; or a nontoxic pharmaceutically acceptable salt thereof, comprising the steps of:

(a) treating a compound of formula III

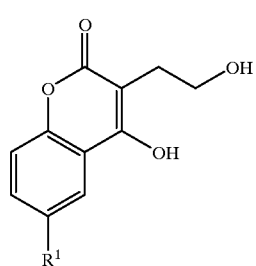

III with an acid to produce a cyclic compound of formula IV

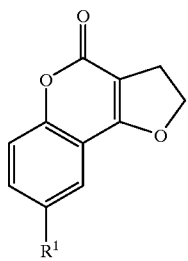

IV wherein $R^1$ is bromo, chloro or nitro;
(b) reacting the compound of formula IV with a substituted aniline of the formula V

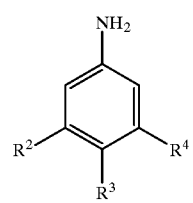

V wherein $R^2$, $R^3$, and $R^4$ are as defined above; to produce a compound of formula VI

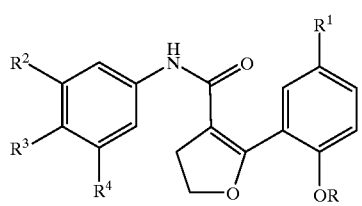

VI wherein $R^1$, $R^2$, $R^3$, and $R^4$ are as defined above and R is hydrogen;
(c) optionally methylating the compound of formula VI wherein R is hydrogen to produce a compound of formula VI wherein R is methyl; and
(d) cyclizing a compound of formula VI wherein R is hydrogen or methyl and $R^1$, $R^2$, $R^3$ and $R^4$ are as defined above by photochemical irradiation to produce the quinoline compound of formula I.

In still another preferred embodiment, the invention provides a process for the preparation of a coumarin compound of formula III

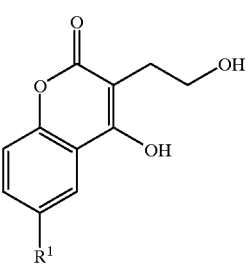

III wherein $R^1$ is bromo, chloro or nitro comprising the step of reacting a compound of formula II

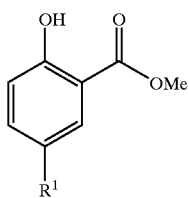

II with γ-butyrolactone and a strong base in an inert organic solvent and then treating the reaction mixture with a strong acid to produce the compound of formula III.

The compounds of Formula I are openers of the large-conductance calcium-activated K⁺ channels (BK channels) which are useful in the treatment of ischemia, stroke, convulsions, asthma, irritable bowel syndrome, migraine, traumatic brain injury, urinary incontinence, and sexual dysfunction in both men (erectile dysfunction, for example, due to diabetes mellitus, spinal cord injury, radical prostatectomy, psychogenic etiology or any other cause) and women by improving blood flow to the genitalia, especially the corpus cavernosum, and other disorders sensitive to BK channel activating activity.

Biological Activity

Potassium ($K^+$) channels are structurally and functionally diverse families of $K^+$-selective channel proteins which are ubiquitous in cells, indicating their central importance in regulating a number of key cell functions [Rudy, B., Neuroscience, 25: 729–749 (1988)]. While widely distributed as a class, $K^+$ channels are differentially distributed as individual members of this class or as families. [Gehlert, D. R., et al., Neuroscience, 52: 191–205 (1993)]. In general, activation of $K^+$ channels in cells, and particularly in excitable cells such as neurons and muscle cells, leads to hyperpolarization of the cell membrane, or in the case of depolarized cells, to repolarization. In addition to acting as an endogenous membrane voltage clamp, $K^+$ channels can respond to important cellular events such as changes in the intracellular concentration of ATP or the intracellular concentration of calcium ($Ca^{2+}$). The central role of $K^+$ channels in regulating numerous cell functions makes them particularly important targets for therapeutic development. [Cook, N. S., Potassium channels: Structure, classification, function and therapeutic potential. Ellis Horwood, Chinchester (1990)]. One class of $K^+$ channels, the large-conductance $Ca^{2+}$-activated $K^+$ channels (Maxi-K or BK channels), is regulated by transmembrane voltage, intracellular $Ca^{2+}$, and a variety of other factors such as the phosphorylation state of the channel protein. [Latorre, R., et al., Ann. Rev. Pysiol., 51: 385–399 (1989)]. The large, single channel-conductance (generally >150 pS) and high degree of specificity for $K^+$ of BK channels indicates that small numbers of channels could profoundly affect membrane conductance and cell excitability. Additionally, the increase in open probability with increasing intracellular $Ca^{2+}$ indicates involvement of BK channels in the modulation of $Ca^{2+}$-dependent phenomena such as secretion and muscular contraction. [Asano, M., et al., J. Pharmacol. Exp. Ther., 267: 1277–1285 (1993)].

Openers of BK channels exert their cellular effects by increasing the open probability of these channels [McKay, M. C., et al., J. Neurophysiol., 71: 1873–1882 (1994); and Olesen, S.-P., Exp. Opin. Invest. Drugs, 3: 1181–1188 (1994)]. This increase in the opening of individual BK channels collectively results in the hyperpolarization of cell membranes, particularly in depolarized cells, produced by significant increases in whole-cell BK-mediated conductance.

The ability of compounds described in the present invention to open BK channels and increase whole-cell outward ($K^+$) BK-mediated currents was assessed under voltage-clamp conditions by determining their ability to increase cloned mammalian (mSlo or hSlo) BK-mediated outward current heterologously expressed in Xenopus oocytes [Butler, A., et al., Science, 261: 221–224 (1993); and Dworetzky, S. I., et al., Mol. Brain Res., 27: 189–193 (1994)]. The two BK constructs employed represent nearly structurally identical homologous proteins, and have proven to be pharmacologically identical in our tests. To isolate BK current from native (background, non-BK) current, the specific and potent BK channel-blocking toxin iberiotoxin (IBTX) [Galvez, A., et al., J. Biol. Chem., 265: 11083–11090 (1990)] was employed at a supramaximal concentration (50 nM). The relative contribution of BK channels current to total outward current was determined by subtraction of the current remaining in the presence of IBTX (non-BK current) from the current profiles obtained in all other experimental conditions (control, drug, and wash). It was determined that at the tested concentration the compounds profiled did not effect non-BK native currents in the oocytes. All compounds were tested in at least 5 oocytes and are reported at the single concentration of 20 μM; the effect of the selected compounds of Formula I on BK current was expressed as the percent of control IBTX-sensitive current and is listed in Table 1. Recordings were accomplished using standard two-electrode voltage clamp techniques [Stuhmer, W., et al., Methods in Enzymology, Vol. 207: 319–339 (1992)]; voltage-clamp protocols consisted of 500–750 ms duration step depolarizations from a holding potential of −60 mV to +140 mV in 20 mV steps. The experimental media (modified Barth's solution) consisted of (in mM): NaCl (88), $NaHCO_3$ (2.4), KCl (1.0), HEPES (10), $MgSO_4$ (0.82), $Ca(NO_3)_2$ (0.33), $CaCl_2$ (0.41); pH 7.5.

TABLE 1

| Ex. No. | BK Current* |
|---------|-------------|
| 4 | ++ |
| 5 | ++ |

*at 20 μM expressed as percent increase over BK current in controls
+ = 100–200%
++ = >200%

To determine the ability of these compounds to reduce cell loss resulting from neuronal ischemia, a standard rodent model of permanent focal ischemia, involving occlusion of the middle cerebral artery in the spontaneously hypertensive rat (middle cerebral artery occlusion (MCAO) model) was employed [Tamura, A., et al., Journal of Cerebral Blood Flow and Metabolism,Volume 1, 53–60, (1981)].

Selected compounds have been evaluated in the focal stroke model involving permanent MCAO in the spontaneously hypertensive rat. This procedure results in a reliably large neocortical infarct volume that is measured by means of vital dye exclusion in serial slices through the brain 24 hours after MCAO. In the present test, compounds were administered using an intravenous route of administration at 2 hours after occlusion. For example, in this model, the compound of Example 5 reduced the cortical infarct volume by about 25% when administered (0.003 mg/kg) as a single bolus 2 hours after middle cerebral artery occlusion as compared to vehicle-treated (2% DMSO, 98% propylene glycol) control.

The in vivo model on erectile function is described fully in the scientific literature (Rehman, J., Chenven, E., Brink, P. Peterson, B., Wolcott, B., Wen, Y. P., Melman, A., Christ, G.: Diminished neurogenic but not pharmacological erections in the 2- to 3-month experimentally diabetic F-344 rat. *Am. J. Physiol.* 272: H1960-H1971, 1997). Briefly, rats (250–600 g) were anesthetized using sodium pentobarbital, the abdomen opened and the cavernous nerve identified. A pressure catheter was placed in the right corpus cavernosum (crus) to measure intracavernous pressure (ICP). A second catheter was introduced into the carotid artery to measure blood pressure. Test compound (0.1, 0.3 and 1 mg/kg i.v.) or vehicle (PEG 400) was given via a catheter placed into the jugular vein.

Control intracavernous pressure responses were elicited by electrically stimulating the cavernous nerve via bipolar stimulating electrodes (20 Hz, 0.22 ms pulse width). Stimulus amplitude (0.2–20 mA) was adjusted to produce a submaximal intracavernous pressure response (typically 0.2 or 0.5 mA). A series of control intracavernous pressure responses were then obtained using a constant stimulus amplitude. Test compound or vehicle was then administered (200 µl i.v bolus) and the cavernous nerve was restimulated to evoke a cavernous pressure response at various times post-drug administration. Animals were excluded from the study if the initial ICP responses to nerve stimulation were unstable ("spiky" responses) or if there were time-dependent variations in the magnitude of the control responses. Animals were also excluded if the control ICP/BP response fell outside the 0.3–0.6 range. A repeated measures ANOVA was used for the evaluation of statistical significance. For example, in this model, the compound of Example 4 (0.1–1 mg/kg) produced an augmentation of the ICP/BP responses elicited by sub-maximal stimulation of the cavernous nerve. A significant increase in the ICP/BP ratio was observed at doses from 0.1–1.0 mg/kg of compound tested.

The results of the above biological tests demonstrates that the compounds of the instant invention are potent openers of the large-conductance calcium-activated $K^+$ channels (Maxi-K or BK channels). Thus, the compounds of the present invention are useful for the treatment of human disorders arising from dysfunction of cellular membrane polarization and conductance and, preferably, are indicated for the treatment of ischemia, stroke, convulsions, epilepsy, asthma, irritable bowel syndrome, migraine, traumatic brain injury, spinal cord injury, sexual dysfunction, urinary incontinence and male erectile dysfunction, other disorders sensitive to BK channel activating activity.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjutants and excipients employing standard and conventional techniques.

The above therapeutic agents, when employed in combination with the compounds of the present invention, may be used, for example, in those amounts indicated in the Physician's Desk Reference (PDR) or as otherwise determined by one of ordinary skill in the art.

However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the scope of the invention.

DESCRIPTION OF SPECIFIC EMBODIMENTS

In the following examples, all temperatures are given in degrees Centigrade. Melting points were recorded on a Gallenkamp capillary melting point apparatus are uncorrected. Proton magnetic resonance ($^1$H NMR) spectra were recorded on a Bruker AC 300 spectrometer. All spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. Infrared (IR) spectra using potassium bromide (KBr) were determined on a Perkin Elmer 781 spectrometer from 4000 $cm^{-1}$ to 400 $cm^{-1}$, calibrated to 1601 $cm^{-1}$ absorption of a polystyrene film and reported in reciprocal centimeters ($cm^{-1}$). Low resolution mass spectra (MS) and the apparent molecular weight $(M+H)^+$ was determined on a Finnigan TSQ 7000. The element analyses are reported as percent by weight.

EXAMPLE 1

3-(2-Hydroxyethyl)-4-hydroxy-6-chlorocoumarin

To a solution of γ-butyrolactone (15.5 g, 178.0 mmol) in THF (100 mL) at −78° C. was added a 1.0 M THF solution of LiHMDS (356 mL, 356 mmol), and the resulting mixture stirred at −78° C. for 1.5 hours. A solution of 5-chlorosalicylic methyl ester (16.6 g, 98% purity, 89.0 mmol) in THF (95 mL) was added. After stirring for 1 hour at 0° C., the mixture was warmed to room temperature overnight to ensure complete reaction. After cooling to 0° C., conc. HCl (12 N, 150 mL) was slowly added to bring the pH to 1. The reaction solution was stirred until HPLC analysis indicated the absence of the keto-ester intermediate. To the mixture was added 400 mL $CH_2Cl_2$ and 300 mL $H_2O$; the organic phase was separated and the aqueous layer was extracted with $CH_2Cl_2$ (100 mL). The organic layers were combined and dried over anhydrous $Na_2SO_4$, and the solvent was removed under reduced pressure to give a solid. Heptane (165 mL) was added to a solution of the solid in THF (290 mL) to crystallize the product. After cooling to 0–5° C. for about 3 hours, the product was isolated by filtration and washed with heptane. After drying in vacuo, a total of 13.9 g (66% yield) of the title compound as off-white crystals was obtained. m.p. 185–186° C.; MS m/z 240;

$^1$H NMR (DMSO-$d_6$, 300 MHz) δ7.84 (d, 1H, J=2.4 Hz), 7.61 (dd, 1H, J=2.4, 8.8 Hz), 7.38 (d, 1H, J=8.8 Hz), 3.56 (t, 2H, J=6.6 Hz), 2.73 (t, 2H, J=6.6 Hz); $^{13}$C NMR (DMSO-$d_6$, 75 MHz) δ162.6, 159.9, 150.5, 131.4, 127.9, 122.4, 118.2, 117.8, 103.2, 59.4, 27.6; IR ($cm^{-1}$) 3247.2, 2945.1, 2458.6, 1664.9, 1623.9, 1572.7, 1311.5, 1378.1, 1070.8, 825.0.

Anal. Calcd. for $C_{11}H_9O_4Cl$: C, 54.90; H, 3.77; Cl, 14.73. Found: C, 54.79; H, 3.70; Cl, 14.76.

EXAMPLE 2

2,3-Dihydro-8-chloro-4H-furobenzopyran-4-one

To a solution of 3-(2-hydroxyethyl)-4-hydroxy-6-chlorocoumarin (Example 1) (8 g, 33.3 mmol) in toluene (360 mL) at room temperature was added p-TSA (0.95 g, 5.0 mmol), and the resulting solution was refluxed with the removal of water using a Dean-Stark condenser. The reaction mixture was cooled to room temperature and washed with saturated sodium bicarbonate solution twice. Toluene was removed by atmospheric distillation to a final volume of 32 mL. After cooling to 70° C., the product started to crystallize. The crystal slurry was held between 55–65° C. for 30 minutes, followed by cooling to 0–5° C. The product was isolated by filtration, washed with cold toluene, and dried in vacuo. A total of 5.5 g (74% yield) of the title compound as off-white crystals was obtained. m.p. 144–146° C.; MS m/z 223 (M+H)$^+$;

$^1$H NMR (CDCl$_3$, 300 MHz) δ7.58 (d, 1H, J=2.5 Hz), 7.49 (dd, 1H, J=2.3, 8.8 Hz), 7.30 (d,1H, J=8.9 Hz), 4.90 (t, 2H, J=9.3 Hz), 3.21 (t, 2H, J=9.5 Hz); $^{13}$C NMR (CDCl$_3$, 75 MHz) δ166.4, 160.3, 153.4, 132.6, 129.6, 122.4, 118.6, 113.8, 103.6, 74.9, 27.1; IR (cm$^{-1}$) 3073.1, 2975.8, 1721.2, 1644.4, 1490.8, 1403.7, 1270.6, 1111.8, 1040.1.

Anal. Calcd. for C$_{11}$H$_7$O$_3$Cl: C, 59.35; H, 3.17; Cl, 15.92. Found: C, 59.13; H, 3.16; Cl, 15.93.

EXAMPLE 3

4-(4'-Trifluoromethylphenylcarboxamide)-5-(2-hydroxy-5-chloro)-2,3-dihydrofuran To a solution of 2,3-dihydro-8-chloro-4H-furobenzopyran-4-one (Example 2) (1.02 g, 4.58 mmol) and 4-(trifluoromethyl)aniline (0.74 g, 4.58 mmol) in THF (50 mL) at −15° C. was added LiHMDS (10.5 mL, 10.5 mmol, 1.0M solution in THF). The clear, red solution was stirred at −15° C. until HPLC analysis indicated<1% of starting material remained (approximately 30 minutes). The reaction mixture was quenched by the addition of an aqueous solution of NaH$_2$PO$_4$ (50 mL, 10 wt % in H$_2$O). After the addition of tert-butyl methyl ether (25 mL), the layers were separated and the rich organic phase washed successively with NaH$_2$PO$_4$ (50 mL, 10 wt % in H$_2$O) and saturated brine solution. After drying over Na$_2$SO$_4$, the solution was concentrated to give the title compound as a clear, orange oil (1.76 g, 100% yield) which crystallized upon refrigeration. Addition of dichloromethane (20 mL) gave white crystals, which were isolated by filtration, washed with dichloromethane (10 mL) and dried to give 1.6 grams of the title compound (90% yield). m.p. 180–180.5° C.; MS m/z 384 (M+H)$^+$;

$^1$H NMR (DMSO-d$_6$, 300 MHz) δ9.76 (s, 1H), 9.34 (s, 1H), 7.76 (d, 2H, J=8.5 Hz), 7.60 (d, 2H, J=8.7 Hz), 7.26 (s, 1H), 7.24 (dd, 1 H, J=2.2, 7.0 Hz), 6.83 (dd, 1H, J=2.4, 7.1), 4.52 (t, 2H, J=9.6 Hz), 3.16 (t, 2H, J=9.6 Hz); $^{13}$C NMR (DMSO-d$_6$, 75 MHz) δ165.5, 159.7, 155.9, 144.7, 132.0, 131.3, 127.3, 123.7, 121.7, 121.2, 119.5, 110.1, 71.5, 32.9; IR (cm$^{-1}$) 3303.6, 2950.2, 1654.6, 1608.5, 1531.7, 1408.8, 1326.9, 1116.9, 1065.7, 840.4.

EXAMPLE 4

4-(5-Chloro-2-hydroxyphenyl)-3-(2-hydroxyethyl)-6-(trifluoromethy)-2(1H)-quinolinone A solution of 4-(4'-trifluoromethylphenylcarboxamide)-5-(2-hydroxy-5-chloro)-2,3-dihydrofuran prepared in Example 3 (1.76 g, 4.58 mmol) in MeOH (500 mL) was purged with nitrogen and irradiated with a 450 W Hanovia lamp at 30–40° C. until HPLC analysis indicated<1% of compound (Example 3) remained. The MeOH was then concentrated in vacuo, and the resulting oil dissolved in dichloromethane (50 mL). Crystals formed after stirring for one hour at room temperature. After cooling the slurry to 0° C., the crystals were isolated by filtration and dried. A total of 0.54 g (30% yield) of the title compound was obtained as a crystalline solid with an HPLC purity of 97 area %. m.p. 253–255° C.; MS m/z 384 (M+H)$^{30}$ ;

$^1$H NMR (DMSO-d$_6$, 300 MHz) δ12.27 (s, 1H), 9.91 (s, 1H), 7.79 (d, 1H, J=8.3 Hz), 7.53 (d, 1H, J=8.5 Hz), 7.42 (dd, 1 H, J=2.4, 8.6 Hz), 7.26(d, 1H, J=2.4 Hz), 7.08 (s, 1H), 7.06 (d, 1H, J=8.9 Hz), 4.60 (m, 1H), 3.44 (m, 2H), 2.50 (m, 2H); $^{13}$C NMR (DMSO-d$_6$, 75 MHz) δ163.7, 155.1, 145.9, 141.7, 132.6, 131.5, 131.3, 127.8, 127.4, 125.5, 124.5, 123.5, 121.0, 119.3, 117.9, 60.7, 33.9.

EXAMPLE 5

4-(5-Chloro-2-methoxyphenyl)-3-(2-hydroxyethyl)-6-(trifluoromethyl)-2(1H)-quinolinone A solution of 4-(4'-trifluoromethylphenylcarboxamide)-5-(2-methoxy-5-chloro)-2,3-dihydrofuran (1.5 g, 3.77 mmol) in MeOH (400 mL) was purged with nitrogen and irradiated with a 450 W Hanovia lamp at 5–26° C. until HPLC analysis indicated<1% of starting material remained. The reaction mixture was then concentrated in vacuo, and the resulting solid was purified by chromatography on silica gel with 3:1 hexane/ethyl acetate. A total of 1.03 g (69% yield) of the title compound was obtained as a white crystalline solid. m.p. 216–217° C.; MS m/z 398 (M+H)$^+$;

$^1$H NMR (DMSO-d$_6$, 300 MHz) δ12.29 (s, 1H), 7.79 (d, 1H, J=8.6 Hz), 7.60 (dd, 1 H, J=2.6, 8.9 Hz), 7.53 (d, 1 H, J=8.6 Hz), 7.37 (d, 1 H, J=2.6 Hz), 7.30 (d, 1H, J=8.9 Hz), 7.00 (s, 1H), 4.59 (m, 1H), 3.69 (s, 3H), 3.40 (m, 2H), 2.50 (m, 2H); $^{13}$C NMR (DMSO-d$_6$, 75 MHz) δ163.6, 156.8, 145.3, 141.7, 132.6, 131.8, 131.5, 127.5, 127.1, 126.3, 124.3, 121.1, 117.9, 115.3, 60.7, 34.0.

What is claimed:

1. A process for preparing a quinoline compound of the formula wherein

R is hydrogen or methyl;

R$^1$ is bromo, chloro or nitro; and

R$^2$, R$^3$ and R$^4$ each are independently hydrogen, halogen, nitro or trifluoromethyl, provided R$^2$, R$^3$, and R$^4$ are not all hydrogen; or a nontoxic pharmaceutically acceptable salt thereof; comprising the steps of:

(a) treating a compound of formula III

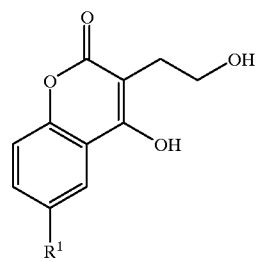

with an acid to produce a cyclic compound of formula IV

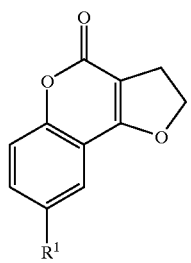

wherein $R^1$ is bromo, chloro or nitro;
(b) reacting the compound of formula IV with a substituted aniline of formula V

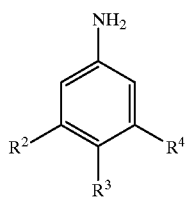

wherein $R^2$, $R^3$, and $R^4$ are as defined above; to produce a compound of formula VI

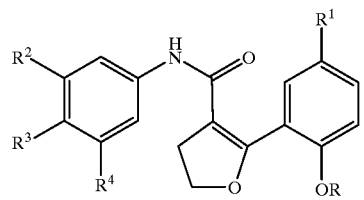

wherein $R^1$, $R^2$, $R^3$, and $R^4$ are as defined above and R is hydrogen;
(c) optionally methylating the compound of formula VI wherein R is hydrogen to produce a compound of formula VI wherein R is methyl; and
(d) cyclizing a compound of formula VI wherein R is hydrogen or methyl and $R^1$, $R^2$, $R^3$, and $R^4$ are as defined above by photochemical irradiation to produce the quinoline compound of formula I.

2. The process of claim 1 further comprising the step of reacting a compound of formula III.

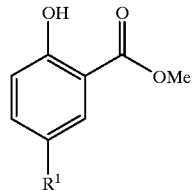

wherein $R^1$ is bromo, chloro or nitro with γ-butyrolactone and a strong base in an inert organic solvent and then treating the reaction mixture with a strong acid to produce the compound of formula III

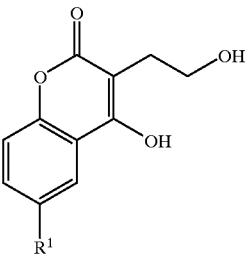

wherein $R^1$ is as defined above.

3. The process of claim 1 wherein $R^1$ is chloro.
4. The process of claim 2 wherein $R^1$ is chloro.
5. The process of claim 3 wherein R, $R^2$ and $R^4$ are hydrogen and $R^3$ is trifluoromethyl.
6. The process of claim 3 wherein R is methyl; $R^2$ and $R^4$ are hydrogen; and $R^3$ is trifluoromethyl.
7. A compound of the formula

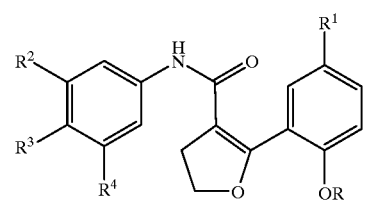

wherein
R is hydrogen or methyl;
$R^1$ is bromo, chloro or nitro; and
$R^2$, $R^3$ and $R^4$ each are independently hydrogen, halogen, nitro or trifluoromethyl, provided $R^2$, $R^3$, and $R^4$ are not all hydrogen.
8. The compound of claim 7 wherein R, $R^2$ and $R^4$ are hydrogen; $R^1$ is chloro; and $R^3$ is trifluoromethyl.
9. The compound of claim 7 wherein $R^2$ and $R^4$ are hydrogen; R is methyl, $R^1$ is chloro; and $R^3$ is trifluoromethyl.

* * * * *